United States Patent
Barrett, Jr. et al.

(10) Patent No.: US 7,433,787 B2
(45) Date of Patent: Oct. 7, 2008

(54) SYSTEM, METHOD, AND COMPUTER PROGRAM PRODUCT USING A DATABASE IN A COMPUTING SYSTEM TO COMPILE AND COMPARE METABOLOMIC DATA OBTAINED FROM A PLURALITY OF SAMPLES

(75) Inventors: Thomas Henry Barrett, Jr., Raleigh, NC (US); Corey Donald DeHaven, Raleigh, NC (US); Danny C. Alexander, Cary, NC (US)

(73) Assignee: Metabolon, Inc., Durham, NC (US)

( * ) Notice: Subject to any disclaimer, the term of this patent is extended or adjusted under 35 U.S.C. 154(b) by 0 days.

(21) Appl. No.: 11/462,838

(22) Filed: Aug. 7, 2006

(65) Prior Publication Data

US 2007/0032969 A1    Feb. 8, 2007

Related U.S. Application Data

(60) Provisional application No. 60/706,459, filed on Aug. 8, 2005.

(51) Int. Cl.
G01N 24/00    (2006.01)
G06F 19/00    (2006.01)

(52) U.S. Cl. ............................ 702/22; 324/308; 600/410

(58) Field of Classification Search .................... 702/19, 702/22, 27, 32, 66–68, 71, 75–77, 189; 324/307–310, 324/312, 316–317; 600/407, 410
See application file for complete search history.

(56) References Cited

U.S. PATENT DOCUMENTS 6,181,134 B1 * 1/2001 Wald .......................... 324/307

6,898,533 B1 * 5/2005 Miller et al. .................. 702/27
7,005,255 B2    2/2006 Kaddurah-Daouk et al.

(Continued)

FOREIGN PATENT DOCUMENTS

WO    WO 2004/106915 A1    12/2004

OTHER PUBLICATIONS

Deshpande et al.; "Automated And Rapid Bacterial Identification Using LC-Mass Spectrometry With A Relational Database Management System" *Computational Systems Bioinformatics Conference*, 2004. CSB 2004, USA.

(Continued)

*Primary Examiner*—Eliseo Ramos-Feliciano
*Assistant Examiner*—Mary C Baran
(74) *Attorney, Agent, or Firm*—Alston & Bird LLP

(57) ABSTRACT

The present invention generates a visual display of metabolomic data compiled by a database and associated processor. More particularly, the present invention provides a database for automatically receiving a three-dimensional spectrometry data set for a group of samples. The present invention also provides a processor device for manipulating the data sets to produce plots that are directly comparable to a plurality of characteristic plots corresponding to a plurality of selected metabolites. Furthermore, the processor device may generate a visual display indicating the presence of the selected metabolites across the group of samples. Thus, the present invention enables a user to analyze a series of complex data sets in a visual display that may indicate the presence of the selected metabolites across the group of samples. Furthermore, the visual display generated by embodiments of the present invention also expedites the subjective analysis of the spectrometry data sets.

7 Claims, 5 Drawing Sheets

U.S. PATENT DOCUMENTS

| | | | |
|---|---|---|---|
| 2001/0016314 A1* | 8/2001 | Anderson et al. | 435/6 |
| 2001/0056485 A1* | 12/2001 | Barrett et al. | 709/224 |
| 2003/0139885 A1* | 7/2003 | Brock et al. | 702/19 |
| 2005/0116159 A1* | 6/2005 | Becker et al. | 250/281 |
| 2005/0209789 A1* | 9/2005 | Hastings | 702/22 |
| 2005/0288872 A1* | 12/2005 | Old et al. | 702/30 |
| 2006/0172429 A1* | 8/2006 | Nilsson et al. | 436/71 |
| 2006/0188868 A1* | 8/2006 | Lloyd et al. | 435/4 |

OTHER PUBLICATIONS

Gamache et al.; "Metabolomic Applications of Electrochemistry/Mass Spectrometry" *J. Am Soc Mass Spectrom*, 2004, pp. 1717-1726, vol. 15, No. 12, USA.

Wagner et al.; "Construction and Application Of A Mass Spectral And Retention Time Index Database Generated From Plant GC/EI-TOF-MS Metabolite Profiles"; *Phytochemistry*, 2003, pp. 887-900, vol. 62, No. 6.

* cited by examiner

SYSTEM, METHOD, AND COMPUTER PROGRAM PRODUCT USING A DATABASE IN A COMPUTING SYSTEM TO COMPILE AND COMPARE METABOLOMIC DATA OBTAINED FROM A PLURALITY OF SAMPLES

CROSS-REFERENCE TO RELATED APPLICATION

This application claims the benefit of U.S. Provisional Application No. 60/706,459, filed Aug. 8, 2005, which is incorporated by reference herein in its entirety.

BACKGROUND OF THE INVENTION

1. Field of the Invention

The present invention relates to the field of metabolomics, which is the study of small molecules produced by an organism's metabolic processes. More particularly, the embodiments of the present invention are adapted to compile and compare metabolomic data received from a spectrometry device across a plurality of samples. Furthermore, embodiments of the present invention may also provide for the display of a visual indication of the presence of selected metabolites in each of the plurality of samples such that metabolomic data may be subjectively analyzed by a user across the plurality of samples.

2. Description of Related Art

Metabolomics is the study of the small molecules, or metabolites, contained in a cell, tissue or organ (including fluids) and involved in primary and intermediary metabolism. The term "metabolome" refers to the collection of metabolites present in an organism. The human metabolome encompasses native small molecules (natively biosynthesizeable, non-polymeric compounds) that are participants in general metabolic reactions and that are required for the maintenance, growth and normal function of a cell. Thus, metabolomics is a direct observation of the status of cellular physiology, and may thus be predictive of disease in a given organism. Subtle biochemical changes (including the presence of selected metabolites) are inherent in a given disease. Therefore, the accurate mapping of these changes to known pathways may allow researchers to build a biochemical hypothesis for a disease. Based on this hypothesis, the enzymes and proteins critical to the disease can be uncovered such that disease targets may be identified for treatment with targeted pharmaceutical compounds.

Molecular biology techniques for uncovering the biochemical processes underlying disease have been centered on the genome, which consists of the genes that make up DNA, which is transcribed into RNA and then translated to proteins, which then make up the small molecules of the human metabolome. While genomics (study of the DNA-level biochemistry), transcript profiling (study of the RNA-level biochemistry), and proteomics (study of the protein-level biochemistry) are useful for identification of disease pathways, these methods are complicated by the fact that there exist over 25,000 genes, 100,000 to 200,000 RNA transcripts and up to 1,000,000 proteins in human cells. However, it is estimated that there may be as few as 2,500 small molecules in the human metabolome.

Thus, metabolomic technology provides a significant leap beyond genomics, transcript profiling, and/or proteomics. With metabolomics, metabolites, and their role in the metabolism may be readily identified. In this context, the identification of disease targets may be expedited with greater accuracy than with any other known methods. The collection of metabolomic data for use in identifying disease pathways is generally known in the art, as described generally in U.S. patent application Ser. No. 10/757,616, entitled Methods for Drug Discovery, Disease Treatment, and Diagnosis Using Metabolomics. Additional uses for metabolomics data are described therein and include, for example, determining response to a therapeutic agent (i.e., drug) or other xenobiotics, monitoring drug response, determining drug safety, and drug discovery. However, the collection and sorting of metabolomic data taken from a variety of biological samples (e.g., from a patient population) consumes large amounts of time and computational power. For example, according to some known metabolomic techniques, spectrometry data for biological samples is collected and plotted in three dimensions and stored in an individual file corresponding to each biological sample. This data is then individually compared to data corresponding to a plurality of known metabolites in order to identify known metabolites that may be disease targets. The data may also be used for identification of toxic agents and/or drug metabolites. Furthermore such data may also be used to monitor the effects of xenobiotics. However, conventional "file-based" methods (referring to the data file generated for each biological sample) require the use of large amounts of computing power and memory assets to handle the screening of large numbers of known metabolites. Furthermore, "file-based" data handling does not lend itself to the compilation of sample population data across a number of samples because, according to known metabolomic data handling techniques, each sample is analyzed independently, without taking into account subtle changes in metabolite composition that may be more readily detectable across a sample population. Furthermore, existing "file-based" method have other limitations including: limited security and audit ability; poor data set consistency across multiple file copies; and individual files do not support multiple indices (example day collected, sample ID, control vs. treated, drug dose, etc) such that all files must be scanned when only a subset is desired.

These limitations in current metabolomic data analysis techniques may lead to the discarding of potentially relevant and/or valuable metabolomic data that may be used to identify and classify particular metabolites as disease targets. Specifically, spectrometry data corresponding to a number of biological samples (such as tissue samples from individual human subjects) generally results in a large data file corresponding to each biological sample, wherein each data file must then be subjected to a screening process using a library of known metabolites. However, conventional systems do not readily allow for the consolidation of spectrometry data from a number of biological samples for the subjective evaluation of the data generated by the spectrometry processes. Thus, while a single file corresponding to an individual sample may be inconclusive, such data may be more telling if viewed subjectively in a succinct format with respect to other samples within a sample population.

Therefore, there exists a need for an improved system to solve the technical problems outlined above that are associated with conventional metabolomic data analysis systems. More particularly, there exists a need for a system capable of automatically receiving spectrometry data without the need to generate a separate data file for each biological sample. There also exists a need for a system capable of converting three-dimensional data sets into a corresponding two-dimensional data set and plot, that may then be compared to a plurality of characteristic plots corresponding to selected metabolites. In addition, there exists a need for a system for allowing a user to subjectively evaluate the spectrometry data across a plurality of samples to identify selected metabolites.

BRIEF SUMMARY OF THE INVENTION

The needs outlined above are met by the present invention which, in various embodiments, also provides a system that overcomes many of the technical problems discussed above, as well other technical problems, with regard to the automated compilation, translation, and concise display of metabolomic data by conventional spectrometry data analysis systems. Specifically, in one embodiment, the system of the present invention compiles and compares metabolomics data received from a analytical device (such as a mass spectrometer) across a plurality of samples in a manner that reduces the burden on computing systems and takes into account metabolomic variance across a sample population. In one embodiment, the system comprises a database in communication with the analytical device for automatically receiving a three-dimensional spectrometry data set corresponding to each of the plurality of samples. A processor device, in communication with the database, may be capable of converting the data set into a corresponding two-dimensional data set and subsequently and/or concurrently plotting the two-dimensional data set. Furthermore, the processor device may also compare the plotted two-dimensional data set to a plurality of characteristic plots corresponding to a plurality of selected metabolites so as to screen the plurality of samples for a presence of the plurality of selected metabolites. According to some embodiments, the system may further comprise a user interface in communication with the database and/or the processor device for displaying a visual indication of the presence of the selected metabolites across the plurality of samples in a succinct graphical format such that a user may subjectively view data from a plurality of samples.

Furthermore, in some system embodiments, the system may further comprise a memory device for storing the plurality of characteristic plots and/or their underlying data sets corresponding to the plurality of selected metabolites. In various system embodiments of the present invention, the database may be used to automatically receive data from various types of analytical devices, including, but not limited to: mass spectrometers (using for example, liquid or gas chromatography techniques); nuclear magnetic resonance (NMR) imaging devices; electrochemical arrays; and/or other analytical devices that may be used to generate metabolomic data from a plurality of biological samples.

Further, the present invention also provides methods and/or computer program products for compiling and comparing metabolomics data across a plurality of samples in a manner that reduces the burden on a computing system. In some embodiments, the method comprises: automatically receiving a three-dimensional spectrometry data set corresponding to each of the plurality of samples in a database; converting the data set into a corresponding two-dimensional data set; plotting the two-dimensional data set; comparing the plotted two-dimensional data set to a plurality of characteristic plots corresponding to a plurality of selected metabolites so as to screen the plurality of samples for a presence of the plurality of selected metabolites; and displaying a visual indication of the presence of the selected metabolites across the plurality of samples.

Method embodiments of the present invention may further comprise compiling the data sets from the plurality of samples into a population data set and indexing the data sets by sample. According to some method embodiments, the displaying a visual indication step may further comprise displaying a plot of a number of each of the plurality of samples versus a characteristic time at which a characteristic intensity peak is recorded. Furthermore, according to some method embodiments, the method may further comprise retrieving the at least one two-dimensional data set corresponding to each of a subset of samples lacking the characteristic intensity peak at the characteristic time and displaying the at least one plotted two-dimensional data set corresponding to each of the subset of samples such that the ostensibly smaller and more manageable subset of samples may be viewed subjectively by a user so as to determine, using both sample population data and/or other statistical methods, whether or not selected metabolites and/or chemical components are present within each sample within the subset of samples.

Thus the systems, methods, and computer program products for compiling and comparing metabolomics data across a plurality of samples, as described in the embodiments of the present invention, provide many advantages that may include, but are not limited to: automatically compiling and indexing complex three-dimensional spectrometry data sets for a plurality of biological samples so as to be capable of generating a sample population data set; converting the complex three dimensional data sets into two dimensional data sets and corresponding data plots that are more easily comparable to a library of data plots corresponding to a plurality of selected metabolites of interest; providing a graphical representation of the spectrometry data analyses used to identify metabolites of interest; and providing a graphical representation of the compiled data across a population of biological samples such that the user of the system of the present invention may subjectively evaluate the spectrometry data and evaluate only those samples exhibiting a variance that may be indicative of the absence and/or presence of a selected metabolite without the need for opening a plurality of individual data files corresponding to each particular biological sample under examination.

These advantages and others that will be evident to those skilled in the art are provided in the system, method, and computer program product of the present invention. Importantly, all of these advantages allow the system to display metabolomic analysis results to a user in a compact format that spans a "fourth dimension" across the population of biological samples. Because, analytical results data spanning across the sample population is made more readily evident to the user in a graphical format, along with the identification of metabolites of interest as potential disease targets, the user is better able to determine the presence and/or absence of selected metabolites and/or chemical components within the samples. Furthermore, because additional sample population data is provided, the embodiments of the present invention are less likely to discount potentially valuable spectrometry results that may be discounted when viewed independently from the sample population.

BRIEF DESCRIPTION OF THE SEVERAL VIEWS OF THE DRAWINGS

Figure 1:
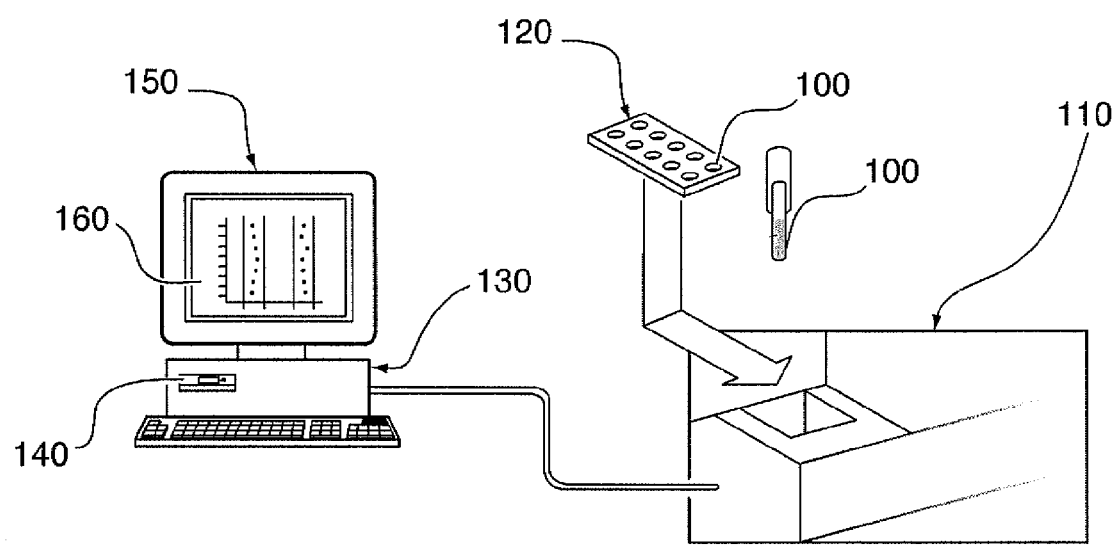
Figure 2A:
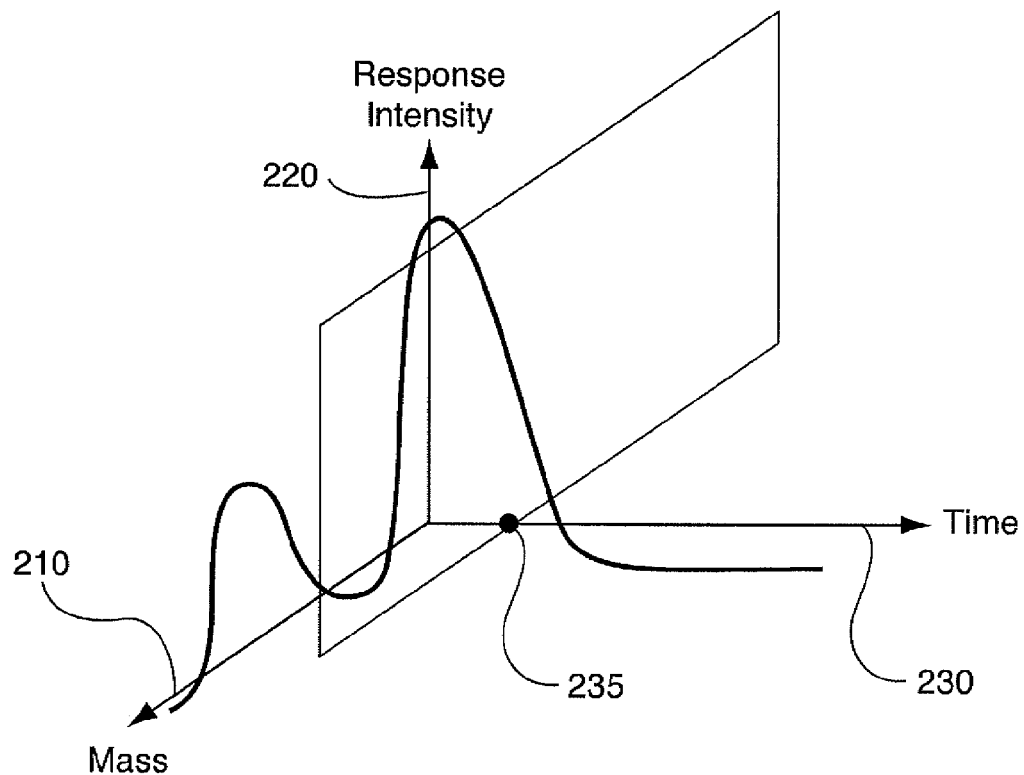
Figure 2B:
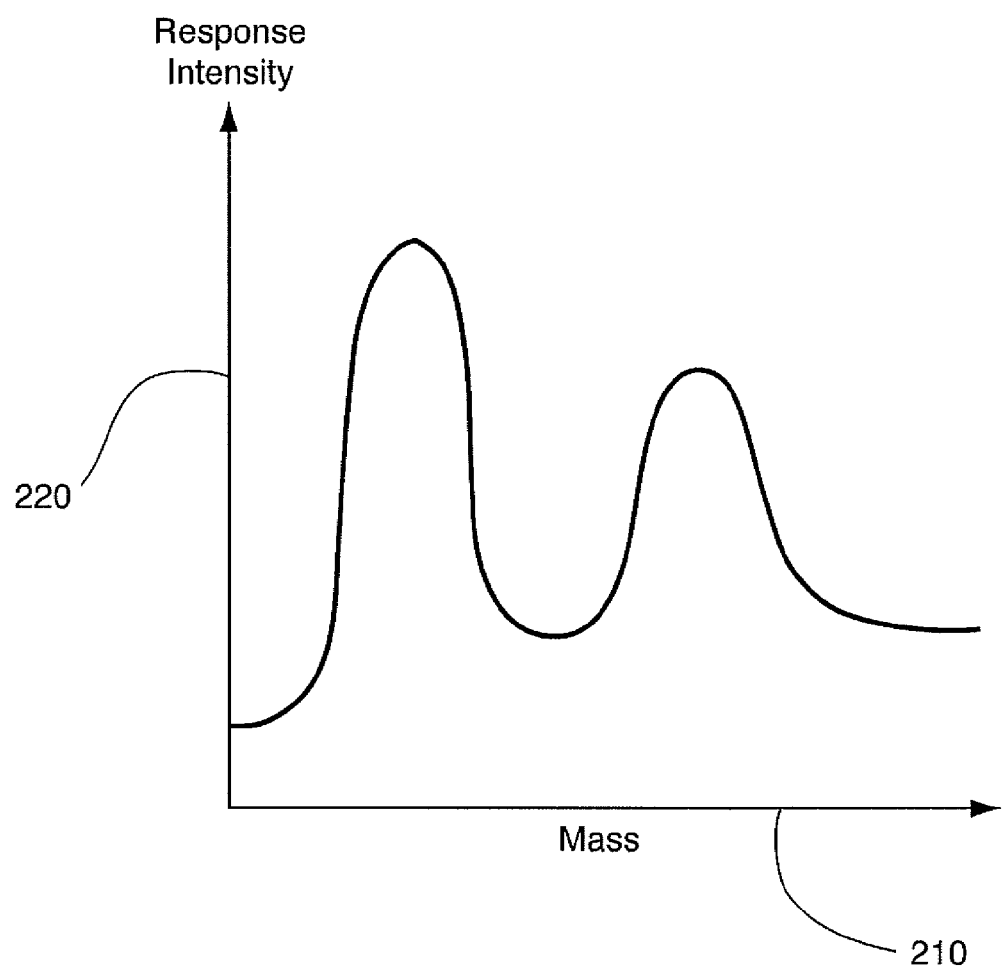
Figure 2C:
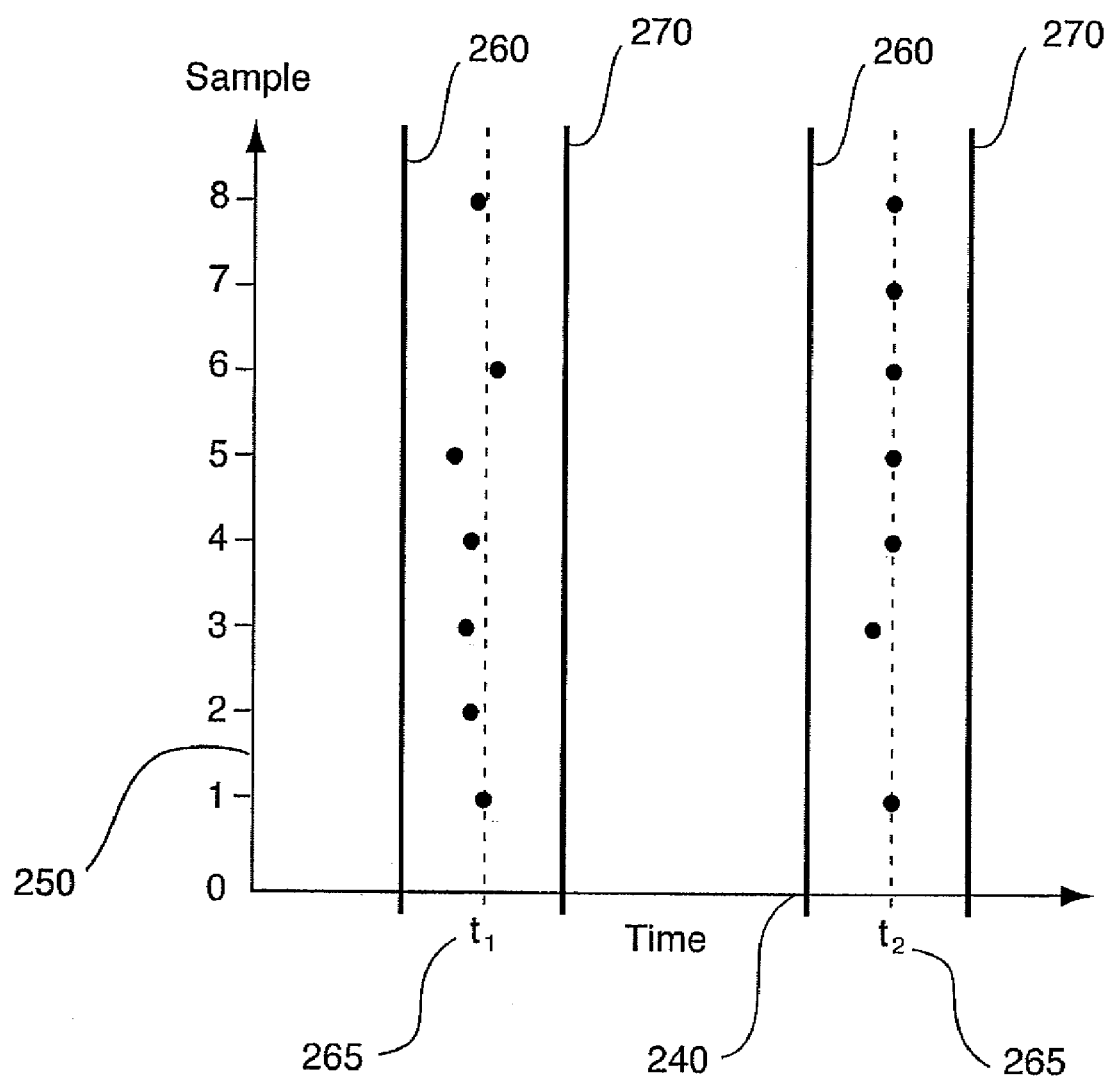
Figure 3:
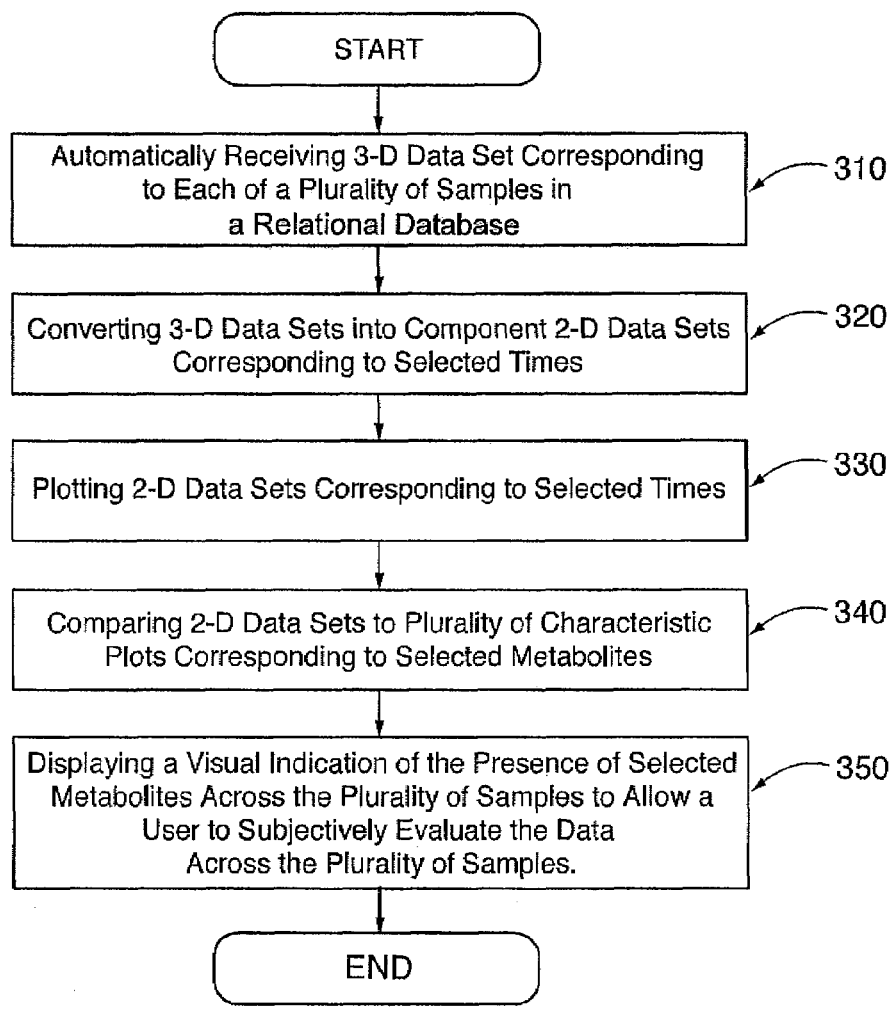

Having thus described the invention in general terms, reference will now be made to the accompanying drawings, which are not necessarily drawn to scale, and wherein:

FIG. 1 illustrates a system according to one embodiment of the present invention including a database, including a memory device and user interface, in communication with a spectrometry device;

FIG. 2a is an illustration of a three-dimensional plot of spectrometry data typically associated with one exemplary biological sample;

FIG. 2b is an illustration of a two-dimensional plot that may be generated by some embodiments of the system of the present invention that may be comparable to a plurality of characteristic plots corresponding to a plurality of selected metabolites;

FIG. 2c is an illustration of a plot that may be generated by some embodiments of the system of the present invention including a visual indication of the presence of the selected metabolites in each of a plurality of samples;

FIG. 3 is an illustration of the operation flow of the systems, methods, and computer program products according to one exemplary embodiment.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The various aspects of the present invention mentioned above, as well as many other aspects of the invention are described in greater detail below. The systems, methods, and computer program products of the present invention are described in conjunction with a mass spectrometer. It must be understood that this is only one example of the use of the present invention. Specifically, the systems, methods, and computer program products of the present invention can be adapted to any number of processes that are used to generate complex sets metabolomic data across a plurality of biological samples. For example, the present invention may be used with a variety of different analytic devices and processes including, but not limited to: nuclear magnetic resonance imaging (NMR); gas chromatography-mass spectrometry (GC-MS); liquid chromatography-mass spectrometry (LC-MS); and electrochemical arrays (EC).

FIG. 1 illustrates an example of a system according to one embodiment of the present invention wherein the system is in communication with an analytical device such as a mass spectrometer 110. As shown, a biological sample 100 may be introduced at the top of a column of media within the spectrometer 110 and analyzed using mass spectrometric techniques that will be appreciated by those skilled in the art. For example, the components of a particular biological sample 100 may pass through the column of the spectrometer at different rates and exhibit different spectral responses based upon their specific characteristics. As will be appreciated by one skilled in the art, the spectrometer 110 may generate a three-dimensional set of spectrometry data corresponding to each biological sample 100 that generally indicates the composition of the biological sample 100. An example of such a three-dimensional set of spectrometry data is shown generally in FIG. 2a, and may be plotted on a three-axis plot including axes for response intensity 220, component mass 210, and time 230 (particularly, in this example, the time a particular component spends in the column of the spectrometer 110). The location of data points relative to the component mass axis 210 may be indicative, for example, of the number of individual component molecules within the biological sample 100 and the relative mass values for such components. According to other embodiments of the system of the present invention, alternate analytical devices may be used to generate a three-dimensional set of analytical data corresponding to the biological sample 100. For example, the analytical device may include, but is not limited to: nuclear magnetic resonance (NMR) imaging devices; liquid and/or gas chromatography-mass spectrometry devices (LC-MS and/or GC-MS); electrochemical array (EC) devices; and/or combinations of these devices. One skilled in the art will appreciate that such complex three-dimensional data sets may be generated by other appropriate analytical devices that may be in communication with components of the system of the present invention as described in further detail below.

A plurality of biological samples 100 may be taken individually from a well plate 120 and/or from other types of sample containers and introduced individually into the analytical device 110 for analysis and generation of the three-dimensional data set (see FIG. 2a). For example, individual biological samples 100 may be transferred from a well plate 120 to the analytical device 110 via pipette, syringe, microfluidic passageways defined in a test array, and/or other systems for transferring biological samples in a laboratory environment. The biological samples may include, but are not limited to: blood samples, urine samples, cell cultures, saliva samples, and/or other types of biological samples in which the metabolites and/or chemical components of interest may be present.

As shown in FIG. 1, the system embodiments of the present invention may comprise a database ((such as a relational database, for example) housed, for example in a memory device 140) in communication with a processor device 130 (such as a computer device, for example) in communication with the analytical device 110 for automatically receiving a three-dimensional data set corresponding to each of the plurality of samples 100. The processor device 130 may be in communication with the analytical device 110 via wire (RS-232, and/or other types of wire connection) and/or wireless (such as, for example, RF, IR, or other wireless communication) techniques such that the database housed therein (and/or in communication therewith) may receive the data set from the analytical device 110. Furthermore, the analytical device 110 may be in communication with one or more processor devices 130 (and associated user interfaces 150) via a wired and/or wireless computer network including, but not limited to: the internet, local area networks (LAN), wide area networks (WAN), or other networking types and/or techniques that will be appreciated by one skilled in the art. The database may be structured using commercially-available software, such as, for example, Oracle, Sybase, DB2, or other database software. As shown in FIG. 1, the database (and/or processor device 130 housing said database) may be in further communication with a memory device 140 (such as a hard drive, memory chip, flash memory, RAM module, ROM module, and/or other memory device 140) for storing three-dimensional data sets automatically received from the analytical device 110. In addition, the memory device 140 may also be used to house the data received by the database and/or manipulated by the processor device 130.

The processor device 130 may, in some embodiments, be capable of converting the three dimensional data set (see FIG. 2a) received by the database 130 into at least one two-dimensional data set (see FIG. 2b) comprising a two-dimensional "profile" of a particular biological sample 100 at a particular point 235 along the time axis (wherein time is measured from a zero point, when the biological sample 100 is injected and/or otherwise introduced into the analytical device 110). For example, the processor device may produce a mass versus intensity profile of the biological sample at a given time point 235 (see FIG. 2b, for example). The "x" axis (or time axis 230, for example) may further be characterized as a retention index and/or a retention time. Thus, the processor device 130 may be further capable of parsing the three-dimensional data set into individual two-dimensional profiles corresponding to particular points (235, for example) in time so as to convert the three-dimensional data set (of FIG. 2a, for example) into at least one two-dimensional data set (having a profile shown, for example, in FIG. 2b) that may further be plotted as an intensity response 220 versus mass 210.

Furthermore, according to some system embodiments, the processor device 130 (in communication with the database) may further systematically compare the at least one plotted two-dimensional data set (as shown, for example, in FIG. 2b) to a plurality of characteristic plots corresponding to a plurality of selected metabolites so as to screen the plurality of biological samples 100 for a presence of the plurality of selected metabolites. As will be appreciated by one skilled in the art, selected known and/or known but "unnamed" metabolites exhibit characteristic mass vs. intensity profiles after a characteristic time spent in a mass-spectrometer 110. Specifically, in some embodiments, the processor device 130 may comprise and/or be in communication with a memory device 140 for storing for storing the plurality of characteristic plots corresponding to the selected metabolites. For example, one skilled in the art will appreciate that metabolites may be identified with varying degrees of certainty by comparing a two-dimensional plot of response intensity (sometimes expressed in µA (as shown in FIG. 2b)) resulting from a mass spectrometry analysis with stored two-dimensional profiles corresponding to selected metabolites. Thus, embodiments of the present invention may be capable of systematically comparing each of the at least one plotted two-dimensional data set (many of which may correspond to each biological sample 100) to a series of characteristic plots corresponding to selected metabolites. It should be understood that the various system and method embodiments of the present invention may be capable of comparing each of the at least one plotted two-dimensional data set to a series of characteristic plots corresponding to selected metabolites, wherein the characteristic plots may correspond to "known named" and/or "known, but unnamed" compounds. For example, embodiments of the present invention are capable of utilizing characteristic plots (stored in a memory device 140, for example) that correspond both to metabolites having chemical names and/or those "known, but unnamed" metabolites for which characteristic plots have been identified, but for which a chemical name and/or classification has not yet been assigned.

Furthermore, because the database of the present invention is capable of storing metabolomic data taken from a plurality biological samples 100 in a single relational database, biological sample 100 data (specifically profile data corresponding to certain selected time points) can be easily combined and/or compared such that the certainty of a "match" between the at least one plotted two-dimensional data set and the characteristic plots of selected metabolites (or other chemicals) may be used to infer the presence of a selected metabolite in a biological sample 100 having a less-certain profile match. Thus, a user of the system of the present invention may subjectively determine that a profile failing to meet the normally-required minimum threshold is actually indicative of the presence of a selected metabolite, given the prevalence of matching profiles within the overall population of biological samples 100. Embodiments of the present invention may thus utilize a visual indication of "certain" matches across a population of biological samples (as shown in FIG. 2c, for example) to infer that uncertain, but likely matches are in fact valid data points and indicative of a "match" that in turn indicates the presence of a selected metabolite and/or chemical component of the biological sample.

For example, the profile shown in FIG. 2b may, in the case of some biological samples 100, match a characteristic plot of a selected metabolite (such as a known metabolite and/or a known, but unnamed metabolite, for example) with near certainty (which may be shown as a data point within a selected time frame 260, 270, as shown in FIG. 2c). However, due to variation in biological samples, potential contaminants within biological samples 100, and/or other experimental complications that will be appreciated by those skilled in the art, the three-dimensional data sets generated by the analysis of some biological samples 100 may result in a two-dimensional mass versus response intensity profile at a given time that does not match a characteristic plot with such certainty. In existing "file-based" data analysis systems, each biological sample 100 is analyzed individually such that the presence of certain metabolites or other chemicals may be unduly and/or prematurely discounted due to the fact that the two-dimensional data set (and corresponding profile plot (as shown in FIG. 2b)) is not capable of being subjectively analyzed in light of a population of biological samples 100.

Embodiments of the system of the present invention, may comprise a user interface 150 in communication with said processor device 130 for displaying a visual indication 160 (see also, FIG. 2c, for example) of the presence of the selected metabolites (as indicated by intensity peaks and certain metabolite "matches") across the plurality of biological samples 100 on a time axis 240 that is indicative of the time at which selected peaks where detected by the analytical device 110. The user interface 150 may be capable of displaying to the user a display 160 of sample number 250 (indicating the identity of the biological sample 100) versus time 240, as shown generally in FIG. 2c.

The user interface 150 may comprise a display device, personal computer, and/or other electronic device having a display for graphical representation of data. For example, as shown in FIG. 2c, a graphical plot of time 240 versus sample number 250 may be generated by the database 130 and displayed via the user interface 150 such that differences in the component makeup of each biological sample may be visually discernable by a user of the system embodiments of the present invention. In some embodiments, the user interface 150 and/or processor device 130 may be capable of generating time threshold markers 260, 270 so that a user may specify visual boundaries on the display 160 (FIG. 2c) in order to readily identify outlying biological samples (for example, Sample #7 as shown in FIG. 2c) that may fail to exhibit intensity peaks that may be detected as clear matches during the selected time frame (as defined by time thresholds 260, 270). Thus, a user of the system of the present invention may utilize the multi-sample visual depiction of FIG. 2c to discern a specific time 265 during which intensity peaks were detected in the majority of biological samples 100. The system of the present invention may then call up specific profile plots (see FIG. 2b, for example) corresponding to the specific time 265 such that a user may then subjectively determine if the profile plot (of mass 210 vs. intensity 220) indicates that the sample does indeed indicate the presence of the selected metabolite (which may be indicated by a less-than-optimal intensity peak for a given characteristic mass).

Furthermore, as shown in FIG. 2c, the system of the present invention may also allow compile and display multiple time thresholds 260, 270 during which peak intensities were objectively determined (by a user and/or system defined threshold)

for each of the biological samples 250. This information may further add to evidence that may be utilized by a user to make the subjective decision to accept a "less than optimal" profile match as indication of the presence of a selected metabolite. For example, as described above, and shown in FIG. 2c, no objective intensity peak for Sample number 7 was detected by the analytical device 110 at time t1. However, objective peaks were detected in all other samples. Thus, the processor device 130 may detect this aberration and automatically display the profile information (see FIG. 2b) to a user via the user interface for Sample number 7 at time t1, such that a subjective user decision may be made to overrule the analytical device 110 objective determination. Furthermore, the system of the present invention also allows a user to further confirm the subjective determination of the presence of an obscured and/or otherwise undetected peak at t1 (for sample 7) by displaying (in the time 240 versus sample 250 plot of FIG. 2c) the presence of an objective "peak" at time t2.

System embodiments of the present invention may thus allow a user to quickly discern which biological samples 100 (displayed on a time plot 160 via a user interface 150) may require further subjective scrutiny. Furthermore, using the time threshold markers 260, 270 in conjunction with the display 160 of the entire population of biological sample 100 results, the processor device 130 of the present invention may then automatically retrieve (from the memory device 140 and/or database 130) the series of at least one two-dimensional plots (see FIG. 2b) corresponding to the biological samples 100 that may not exhibit "match" or characteristic intensity peaks at the selected times 265 when compared to the overall population of biological samples. The two dimensional plots retrieved from the database (corresponding to the outlying points 280) may then be subjectively analyzed to determine if the absence of a characteristic peak at the selected time 265 is indicative of a lack and/or presence of selected metabolites that may differ from the chemical makeup of the majority of the population of biological samples 100.

Some system embodiments may thus generate a listing of one or more metabolites present in the biological samples as visually discernable from the overall population of biological samples 100 in the graphical display 150 shown, for example, in FIG. 2c. The listing of metabolites may thus provide a corresponding list of disease targets for pharmaceutical development. In addition, in some embodiments, the processor device 130, in communication with the database, may also be used to map clinical data including, but not limited to: symptoms exhibited by patients from whom the biological samples 100 have been taken; known disease states of the patients from whom the biological samples 100 have been taken; patient physiological data; other supplemental patient data (height, weight, age, etc.); and/or other clinical data. Thus, using the database of the present invention, other clinical factors may be correlated with the presence of selected metabolites in a biological sample 100 such that the database 130 may be used to generate predictive tests for diseases and/or disorders that may result in characteristic and measurable changes in metabolomic data.

Embodiments of the present invention also include a method for compiling and comparing metabolomics data across a plurality of biological samples 100, as shown generally in the flow diagram of FIG. 3. Step 310 comprises automatically receiving a three-dimensional data set (such as that shown graphically in FIG. 2a) corresponding to each of the plurality of biological samples 100 in a database. As shown generally in FIG. 1, and as described above, the three-dimensional data set may comprise spectrometry data received by the database which may be in communication (via wired and/or wireless connection) with a processor device 130 (such as a computer device) and an analytical device 110 capable of generating characteristic analytic data corresponding to a biological sample 100 containing a plurality of metabolites and other components. In some embodiments, wherein the three-dimensional data set is generated using mass-spectrometry, the axes defining the three-dimensional data set may comprise, as shown generally in FIG. 2a: component mass 210, response intensity 220, and time 230 (wherein time refers to the time a particular component of the biological sample 100 spends in the column of the spectrometer 110). Furthermore, the automatic receiving step 310 may be repeated for a number of biological samples 100 in a population of samples and automatically compiled by the processor device 130 of the present invention such that analytical data corresponding to each biological sample 100 is indexed and remains retrievable from the database by the processor device 130 (and/or a computer device or user interface 150 in communication therewith).

More specifically, in some method embodiments, the automatic receiving step 310 may further comprise: compiling the three-dimensional data from a plurality of biological samples 100 in order to generate a population data set (that may be used to further determine the statistical boundaries of the sample population); and indexing the three-dimensional data according to the individual biological sample 100 such that as statistical outliers (see sample 7 at FIG. 2c, for example) among the biological samples 100 are identified relative to the overall population, the data corresponding to the particular biological samples 100 (i.e., sample 7) may be retrieved from the database by the processor device 130 and displayed to a user (via a user interface 150, for example) for a subjective determination of whether selected metabolites are present in those biological samples 100. As described above, the system of the present invention may be used to define time thresholds (see elements 260, 270 of FIG. 2c) such that the database 130 may retrieve data corresponding to biological samples 100 exhibiting a selected variance from the sample population.

Step 320 of the method embodiments of the present invention comprises converting the three-dimensional data set (shown generally in FIG. 2a) into at least one corresponding two-dimensional data set (shown generally in FIG. 2b). Step 320 may comprise, for example, parsing the three-dimensional data set along the time axis 220 such that each component of the biological sample 100 having a different time may be associated with a corresponding two-dimensional data set plotted as response intensity 220 versus mass 210 (see FIG. 2b). Method embodiments of the present invention may also comprise Step 330 for plotting the at least one two-dimensional data set as shown in FIG. 2b. For example, in method embodiments wherein spectrometry data is automatically received by the database in step 310, step 330 may comprise plotting the two-dimensional data set (corresponding to a biological sample 100 component having characteristic time of detection within a spectrometer column, for example) relative to mass 210 and response intensity 220 axes that may be directly comparable to characteristic plots corresponding to selected metabolites. Thus, method step 340 comprises comparing the at least one plotted two-dimensional data set (see FIG. 2b, for example) to a plurality of characteristic plots corresponding to a plurality of selected metabolites so as to screen the plurality of samples 100 for a presence of the plurality of selected metabolites.

One skilled in the art will appreciate that such 2-dimensional profiles may be indicative of the presence and/or absence of a particular metabolite and/or other chemical component within a biological sample 100 subjected to mass spectrometry. However, one skilled in the art will also appreciate that only a certain percentage of biological samples produce mass versus response intensity profiles that indicate a certain match with a selected metabolite. Method embodiments of the present invention may also comprise Step 330 for plotting the at least one two-dimensional data set as shown in FIG. 2b. For example, in method embodiments wherein spectrometry data is automatically received by the database in step 310, step 330 may comprise plotting the two-dimensional data set (corresponding to a biological sample 100 component having a particular mass, for example) relative to time 230 and response intensity 220 axes that may be directly comparable to characteristic plots corresponding to selected metabolites. Thus, method step 340 comprises comparing the at least one plotted two-dimensional data set (see FIG. 2b, for example) to a plurality of characteristic plots corresponding to a plurality of selected metabolites so as to screen the plurality of samples 100 for a presence of the plurality of selected metabolites. As described herein with respect to the various system embodiments of the present invention, it should be understood that the method embodiments may also be capable of comparing each of the at least one plotted two-dimensional data set to a series of characteristic plots corresponding to selected metabolites that may include, but are not limited to: "known and named metabolites," and/or "known, but unnamed" metabolites. For example, various method embodiments described herein are capable of utilizing characteristic plots that correspond both to metabolites having chemical names and/or those "known, but unnamed" metabolites for which characteristic plots have been identified, but for which a chemical name and/or classification has not yet been assigned.

As shown in FIG. 3, Step 350 comprises displaying a visual indication of the presence of the selected metabolites in each of the plurality of samples 100. According to some embodiments, this method step may further comprise: generating a graphical display (as shown in FIG. 2c) of time 240 (i.e., time of detection of an objective matching intensity "peak") versus sample number 250 to first identify biological samples 100 having a lack of characteristic peaks within a selected time period (as defined by, for example, time thresholds 260, 270) when compared to the overall sample population; and retrieving the at least one two-dimensional data set corresponding to the biological samples 100 exhibiting a lack of characteristic peaks such that a user may make a subjective determination of the presence of a selected metabolite and/or chemical component. Finally, step 350, may, in some embodiments, further comprise providing a listing of metabolites and/or chemical components that are present in the biological samples 100.

Thus, the method embodiments of the present invention may allow for the subjective determination of the presence and/or absence of a selected metabolite and/or chemical component within a biological sample 100 by linking data from a population of biological samples in a database such that as characteristic data sets (as plotted in FIG. 2b) are accumulated for each biological sample, these data sets may be linked and utilized to map characteristic data across the plurality of biological samples 100 (as plotted, for example in FIG. 2c). The visual indication of FIG. 2c may thus allow for the easy identification of specific biological samples that may require subjective scrutiny. This may be especially apparent in FIG. 2c, for example, when a particular sample does not exhibit characteristic peaks and/or profile matches at each time of interest 265, but does conform to the overall population data in other respects. While previous data analysis methods may have discounted and/or discard such samples 100, the method of the present invention allows a user to highlight such biological samples for closer subjective scrutiny such that aberrations may be either explained and/or ruled as indicative of a fundamental chemical difference in the sample.

In addition to providing apparatus and methods, the present invention also provides computer program products for performing the operations described above. The computer program products have a computer readable storage medium having computer readable program code means embodied in the medium. With reference to FIG. 3, the computer readable storage medium may be part of the memory device 140, and may implement the computer readable program code means to perform the above discussed operations.

In this regard, FIG. 3 is a block diagram illustration of methods, systems and program products according to the invention. It will be understood that each block or step of the block diagram and combinations of blocks in the block diagram can be implemented by computer program instructions. These computer program instructions may be loaded onto a computer or other programmable apparatus to produce a machine, such that the instructions which execute on the computer or other programmable apparatus create means for implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for compiling and comparing metabolomics data received from an analytical device across a plurality of samples, the system comprising:

a database in communication with the analytical device, said database being configured to automatically receive from the analytical device a three-dimensional data set corresponding to each of the plurality of samples;

a processor device in communication with said database, said processor device being configured to:

convert the three-dimensional data set into at least one two-dimensional data set for each of the plurality of samples;

plot the at least one two-dimensional data set for each of the plurality of samples;

compare the at least one plotted two-dimensional data set for each of the plurality of samples to a plurality of characteristic plots corresponding to a plurality of selected metabolites so as to screen the plurality of samples by associating at least one of the plurality of selected metabolites with the at least one plotted two-dimensional data set for each of the plurality of samples; and compare, for the screened plurality of samples determined to have the at least one of the plurality of selected metabolites associated therewith, the at least one plotted two-dimensional data set for each of the screened plurality of samples, across the screened plurality of samples, so as to determine a trend of the associated at least one of the plurality of selected metabolites, across the screened plurality of samples; and a user interface in communication with said database and said processor device, the user interface being configured to display a visual indication of the comparison of the at least one plotted two-dimensional data set for each of the screened plurality of samples, across a plurality of the screened plurality of samples, to visually indicate the screened plurality of samples determined to have the at least one of the plurality of selected metabolites associated therewith, and the trend corresponding thereto, across the plurality of the screened plurality of samples.

2. A system according to claim 1, further comprising a memory device in communication with said database, the memory device being configured to store the plurality of characteristic plots.

3. A system according to claim 1, wherein the analytical device is at least one of:

a nuclear magnetic resonance imaging device;

a spectrometry device;

an electrochemical array device; and combinations thereof.

4. A method for compiling and comparing metabolomics data across a plurality of samples, the method comprising:

automatically receiving, in a database, a three-dimensional data set corresponding to each of the plurality of samples;

converting the three-dimensional data set into at least one corresponding two-dimensional data set for each of the plurality of samples;

plotting the at least one two-dimensional data set for each of the plurality of samples;

comparing the at least one plotted two-dimensional data set for each of the plurality of samples to a plurality of characteristic plots corresponding to a plurality of selected metabolites so as to screen the plurality of samples by associating of at least one of the plurality of selected metabolites with the at least one plotted two-dimensional data set for each of the plurality of samples;

comparing, for the screened plurality of samples determined to have the at least one of the plurality of selected metabolites associated therewith, the at least one plotted two-dimensional data set for each of the screened plurality of samples, across the screened plurality of samples, so as to determine a trend of the associated at least one of the plurality of selected metabolites, across the screened plurality of samples; and displaying a visual indication of the comparison of the at least one plotted two-dimensional data set for each of the screened plurality of samples, across a plurality of the screened plurality of samples, to visually indicate the screened plurality of samples determined to have the at least one of the plurality of selected metabolites associated therewith, and the trend corresponding thereto, across the plurality of the screened plurality of samples.

5. A method according to claim 4, wherein the automatically receiving step further comprises:

compiling the three-dimensional data sets from the plurality of samples into a population data set; and indexing the three-dimensional data sets by sample.

6. A method according to claim 4, wherein the visual indication comprises a plot of corresponding ones of the at least one plotted two-dimensional data set for each of the plurality of the screened plurality of samples versus a characteristic time at which a characteristic intensity peak of the at least one of the plurality of selected metabolites is expected.

7. A method according to claim 6, further comprising retrieving the at least one plotted two-dimensional data set corresponding to each of a subset of samples lacking the characteristic intensity peak of the at least one of the plurality of selected metabolites at the characteristic time; and displaying the at least one plotted two-dimensional data set corresponding to each of the subset of samples for subjective evaluation.

* * * * *